US010952749B2

United States Patent
Abbasi

(10) Patent No.: US 10,952,749 B2
(45) Date of Patent: Mar. 23, 2021

(54) SURGICAL TOOLS HAVING APPLICATION FOR SPINAL SURGICAL PROCEDURES AND METHOD OF USE

(71) Applicant: Hamid R. Abbasi, Edina, MN (US)

(72) Inventor: Hamid R. Abbasi, Edina, MN (US)

(73) Assignee: Advance Research System, LLC, Edina, MN (US)

( * ) Notice: Subject to any disclaimer, the term of this patent is extended or adjusted under 35 U.S.C. 154(b) by 310 days.

(21) Appl. No.: 15/773,495

(22) PCT Filed: Nov. 11, 2016

(86) PCT No.: PCT/US2016/061535
§ 371 (c)(1),
(2) Date: May 3, 2018

(87) PCT Pub. No.: WO2017/083653
PCT Pub. Date: May 18, 2017

(65) Prior Publication Data
US 2018/0317938 A1 Nov. 8, 2018

Related U.S. Application Data

(63) Continuation of application No. 14/941,046, filed on Nov. 13, 2015, now Pat. No. 9,675,363.

(51) Int. Cl.
*A61B 17/16* (2006.01)
*A61B 17/34* (2006.01)
(Continued)

(52) U.S. Cl.
CPC ...... *A61B 17/1637* (2013.01); *A61B 17/1659* (2013.01); *A61B 17/1671* (2013.01); *A61B 17/1757* (2013.01); *A61B 17/320016* (2013.01); *A61B 17/3417* (2013.01); *A61B 17/3421* (2013.01); *A61B 17/3468* (2013.01); *A61B 17/7032* (2013.01); *A61B 17/7035* (2013.01);
(Continued)

(58) Field of Classification Search
CPC ............ A61B 17/1637; A61B 17/3417; A61B 17/1697
See application file for complete search history.

(56) References Cited

U.S. PATENT DOCUMENTS 4,969,888 A 11/1990 Scholten et al.
6,436,119 B1 8/2002 Erb et al.
(Continued)

FOREIGN PATENT DOCUMENTS

WO WO2009/046414 A1 4/2009

*Primary Examiner* — Olivia C Chang
(74) *Attorney, Agent, or Firm* — Christensen, Fonder, Dardi & Herbert PLLC

(57) ABSTRACT

A cannula tool in combination with other tools is used to provide multiple instruments necessary for surgical procedures. The cannula tool is used in combination with a piercing tool to form a dilator instrument to access a treatment site and in combination with a plunger tool to deliver biological or grafting material to a treatment site. Each of the plunger and piercing tools includes a guide lumen to track the tools over a K-wire or other guide device for placement at the treatment site. The application discloses asymmetrical piercing and plunger tools for placement proximate to a facet joint for treatment.

5 Claims, 15 Drawing Sheets

(51) Int. Cl.
　　*A61B 17/32* (2006.01)
　　*A61B 17/70* (2006.01)
　　*A61B 17/17* (2006.01)
　　*A61B 17/88* (2006.01)
　　*A61B 17/02* (2006.01)
　　*A61B 17/22* (2006.01)
　　*A61B 17/84* (2006.01)

(52) U.S. Cl.
　　CPC ........ *A61B 17/8897* (2013.01); *A61B 17/848* (2013.01); *A61B 2017/0256* (2013.01); *A61B 2017/22039* (2013.01); *A61B 2017/3454* (2013.01)

(56) References Cited

U.S. PATENT DOCUMENTS

| | | | |
|---|---|---|---|
| 7,799,032 B2 | 9/2010 | Assell et al. | |
| 7,909,872 B2 | 3/2011 | Zipnick et al. | |
| 8,414,606 B2 | 4/2013 | Shadeck et al. | |
| 8,496,709 B2 | 7/2013 | Schell et al. | |
| 8,814,914 B2 | 8/2014 | Miller et al. | |
| 8,876,851 B1 | 11/2014 | Woolley et al. | |
| 9,072,551 B2 | 7/2015 | Paroth et al. | |
| 9,119,645 B2 | 9/2015 | McBride | |
| 9,119,684 B2 | 9/2015 | Fallin et al. | |
| 9,155,572 B2 | 10/2015 | Altarac et al. | |
| 2007/0255208 A1 | 11/2007 | McMichael et al. | |
| 2009/0138043 A1 | 5/2009 | Kohm | |
| 2009/0149857 A1 | 6/2009 | Culbert et al. | |
| 2009/0157044 A1 | 6/2009 | Liyanagama et al. | |
| 2010/0023006 A1 | 1/2010 | Ellman | |
| 2011/0202062 A1 | 8/2011 | O'Halloran et al. | |
| 2012/0123473 A1* | 5/2012 | Hernandez | A61B 17/0401 606/232 |
| 2012/0316500 A1 | 12/2012 | Bierman et al. | |
| 2013/0046200 A1 | 2/2013 | Stauber | |

* cited by examiner

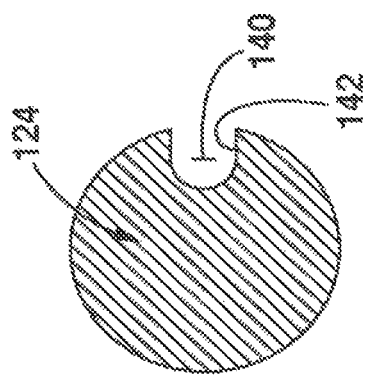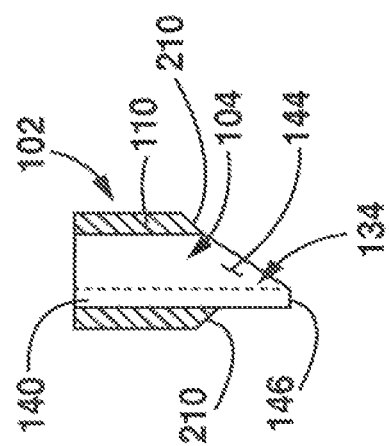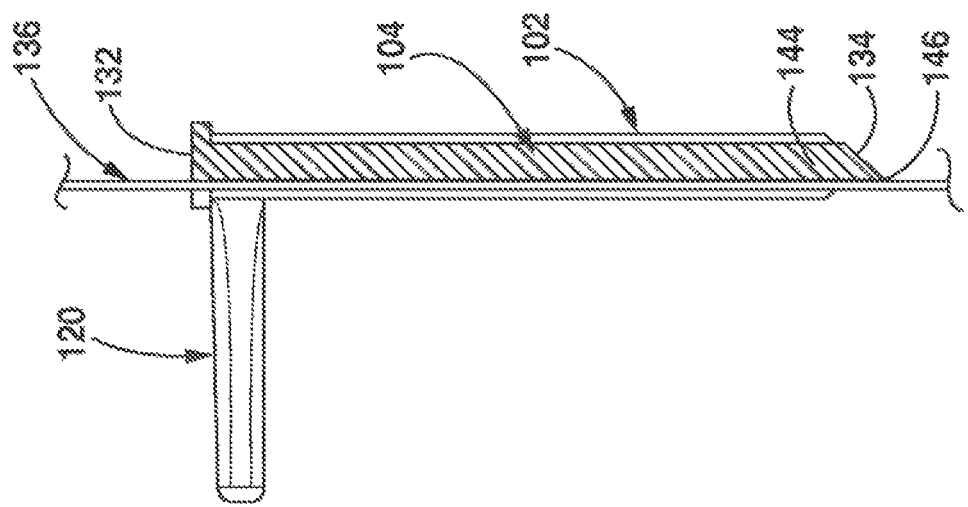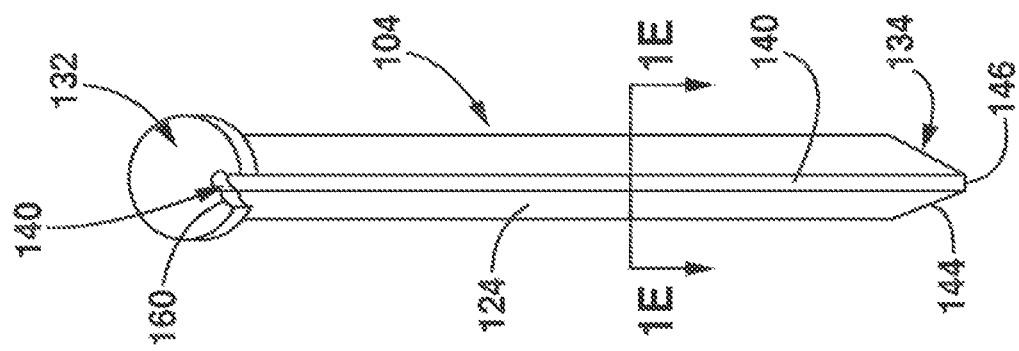

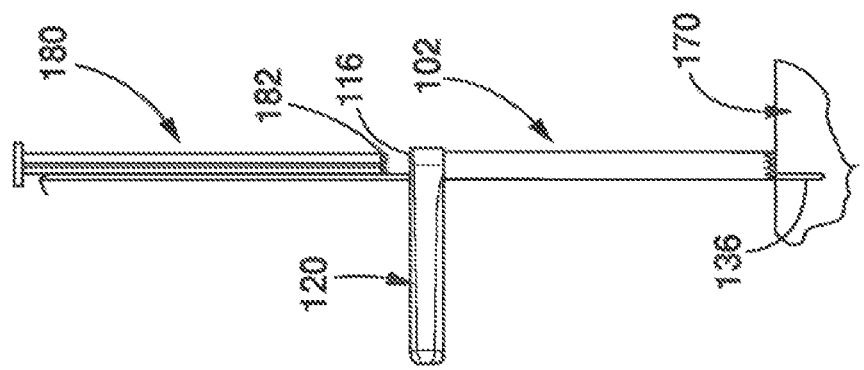
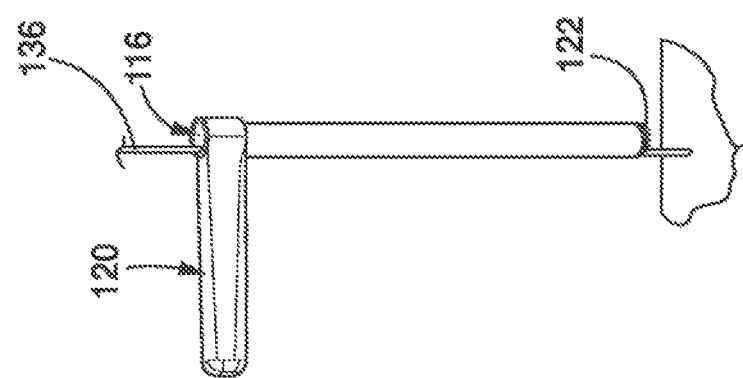
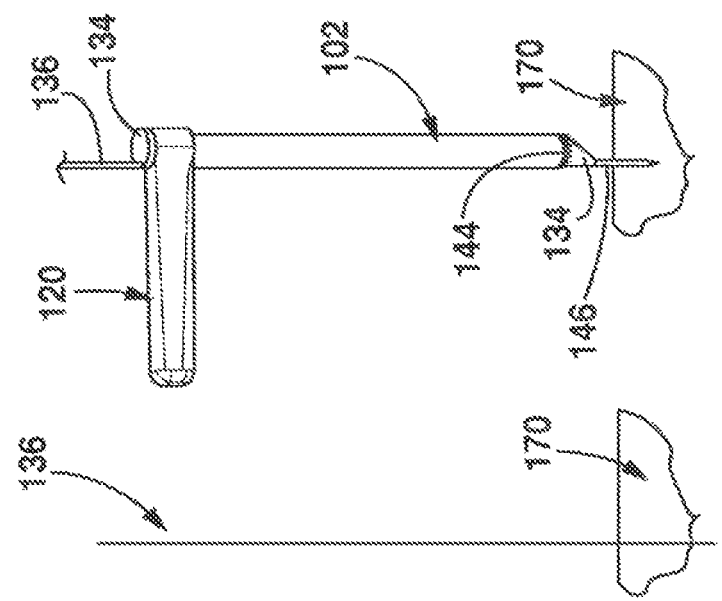
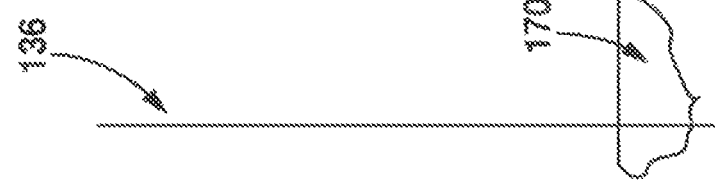

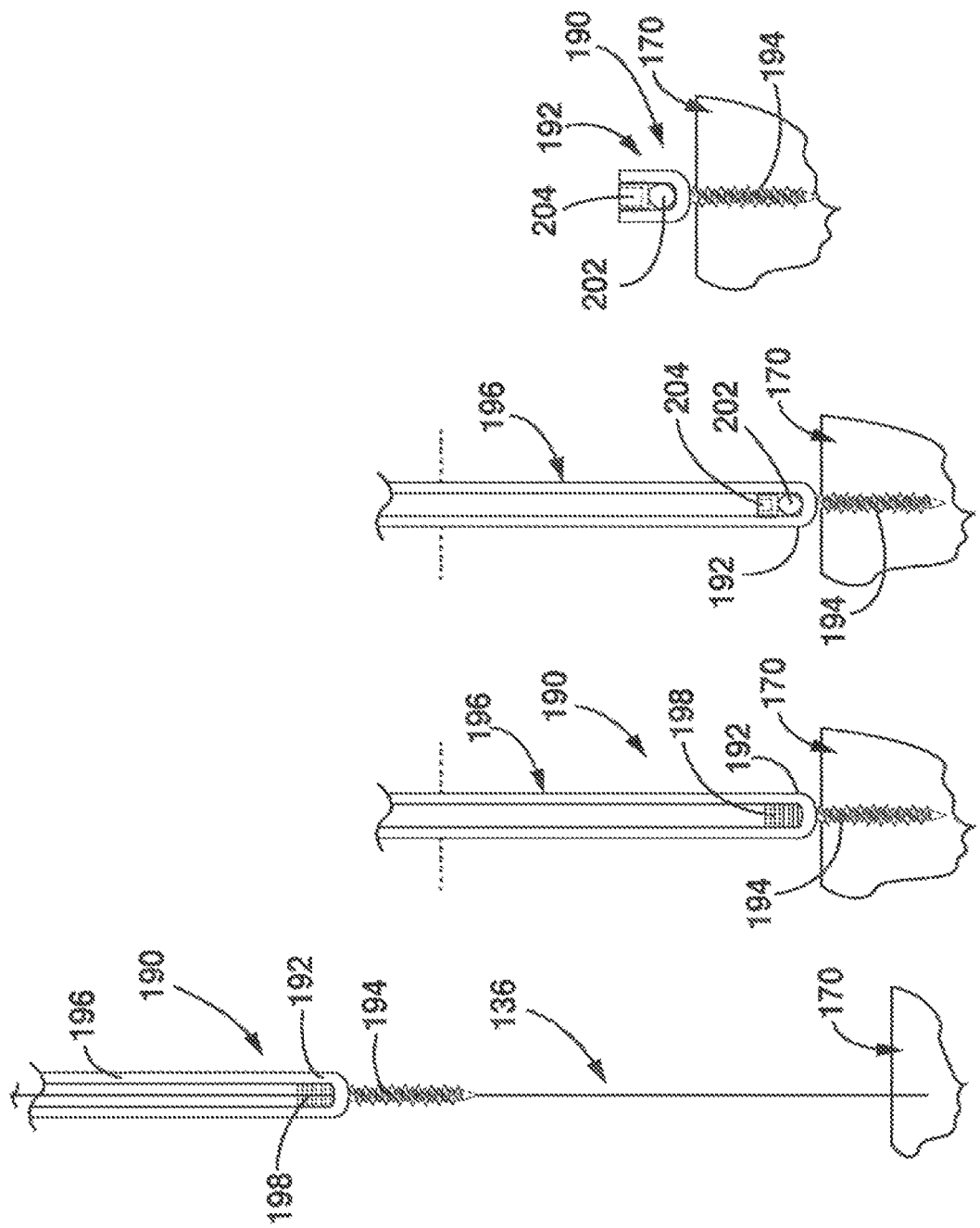

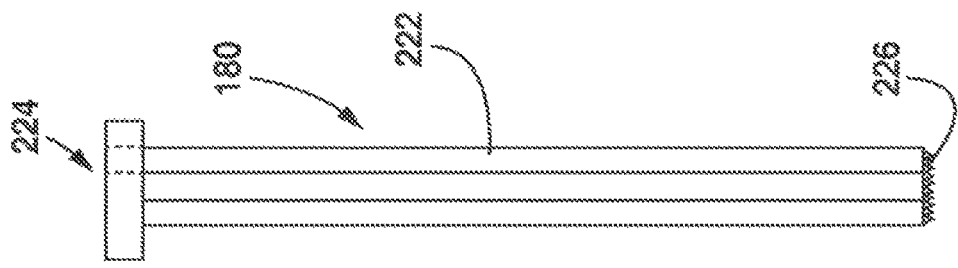
FIG. 4A
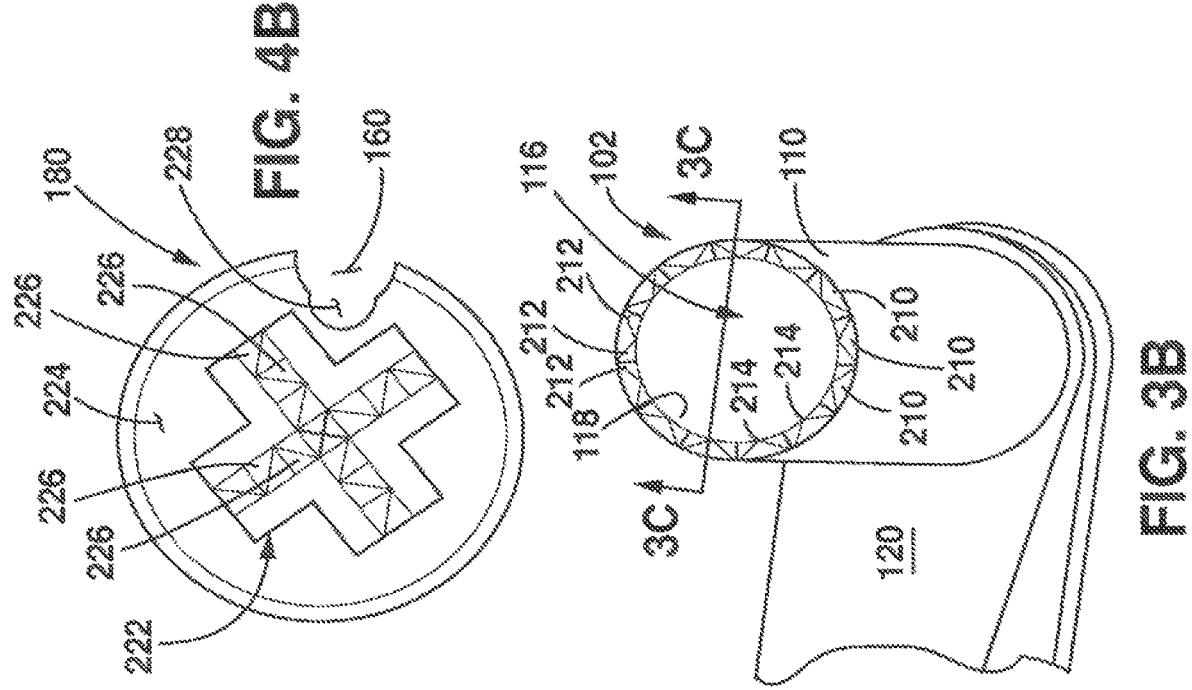
FIG. 4B
FIG. 3B
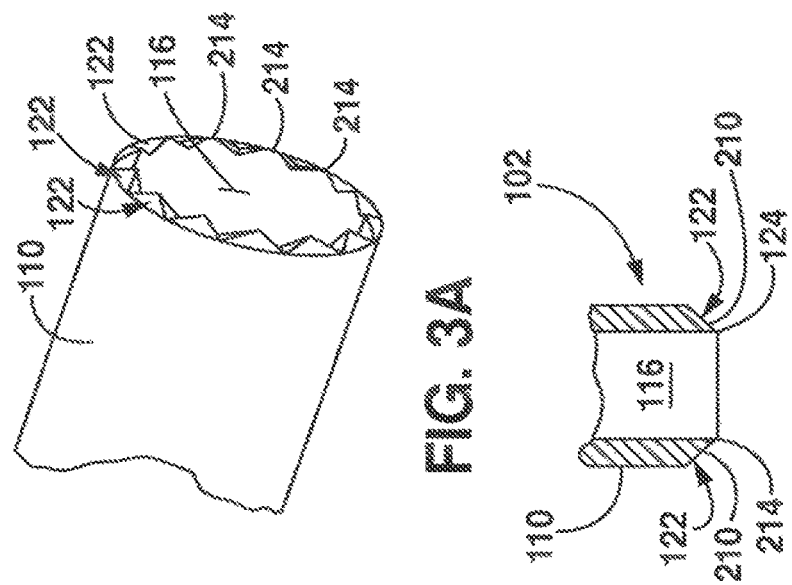
FIG. 3A
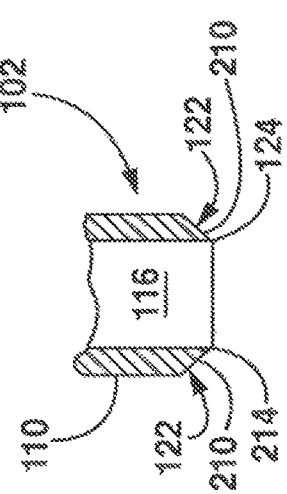
FIG. 3C

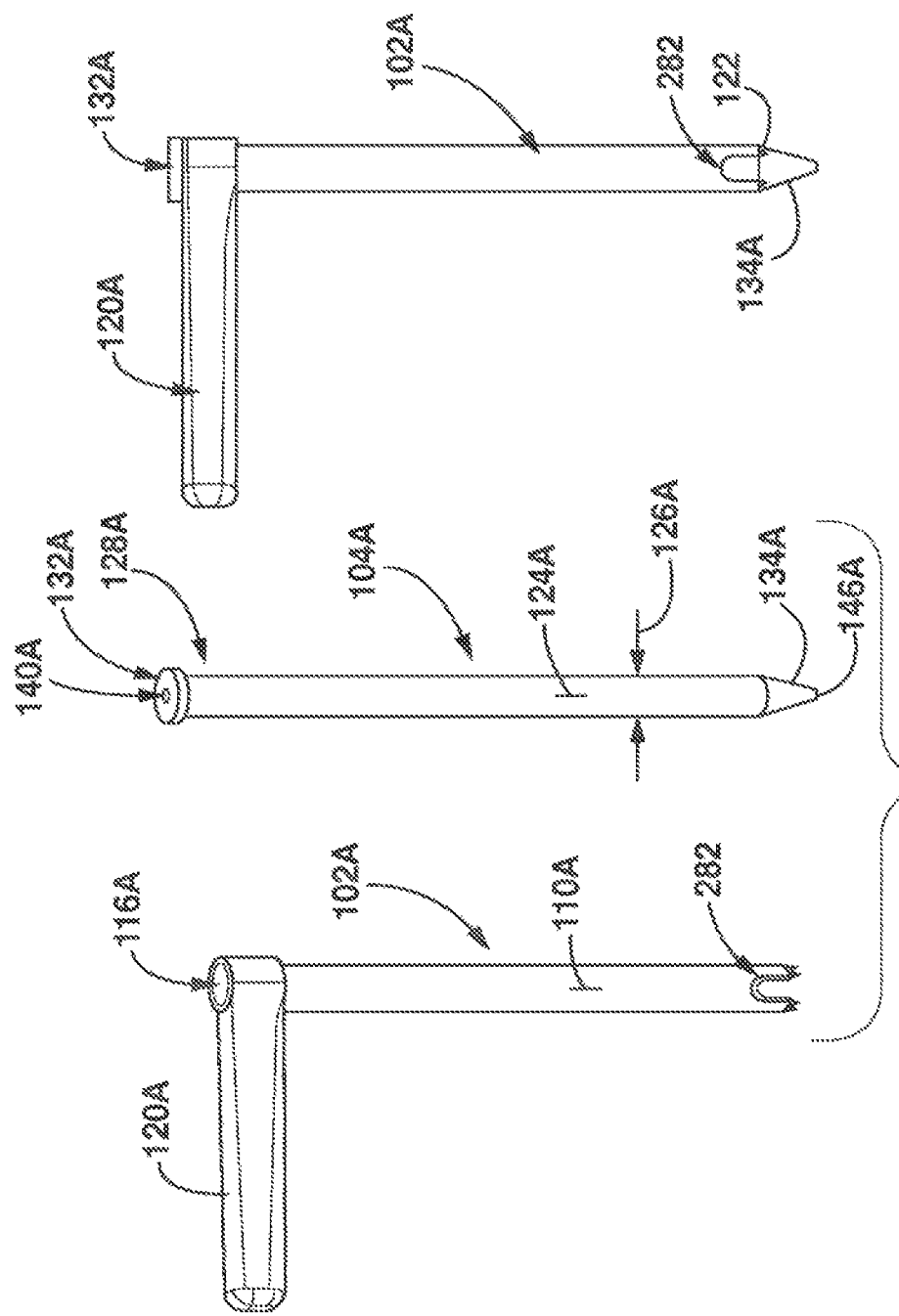

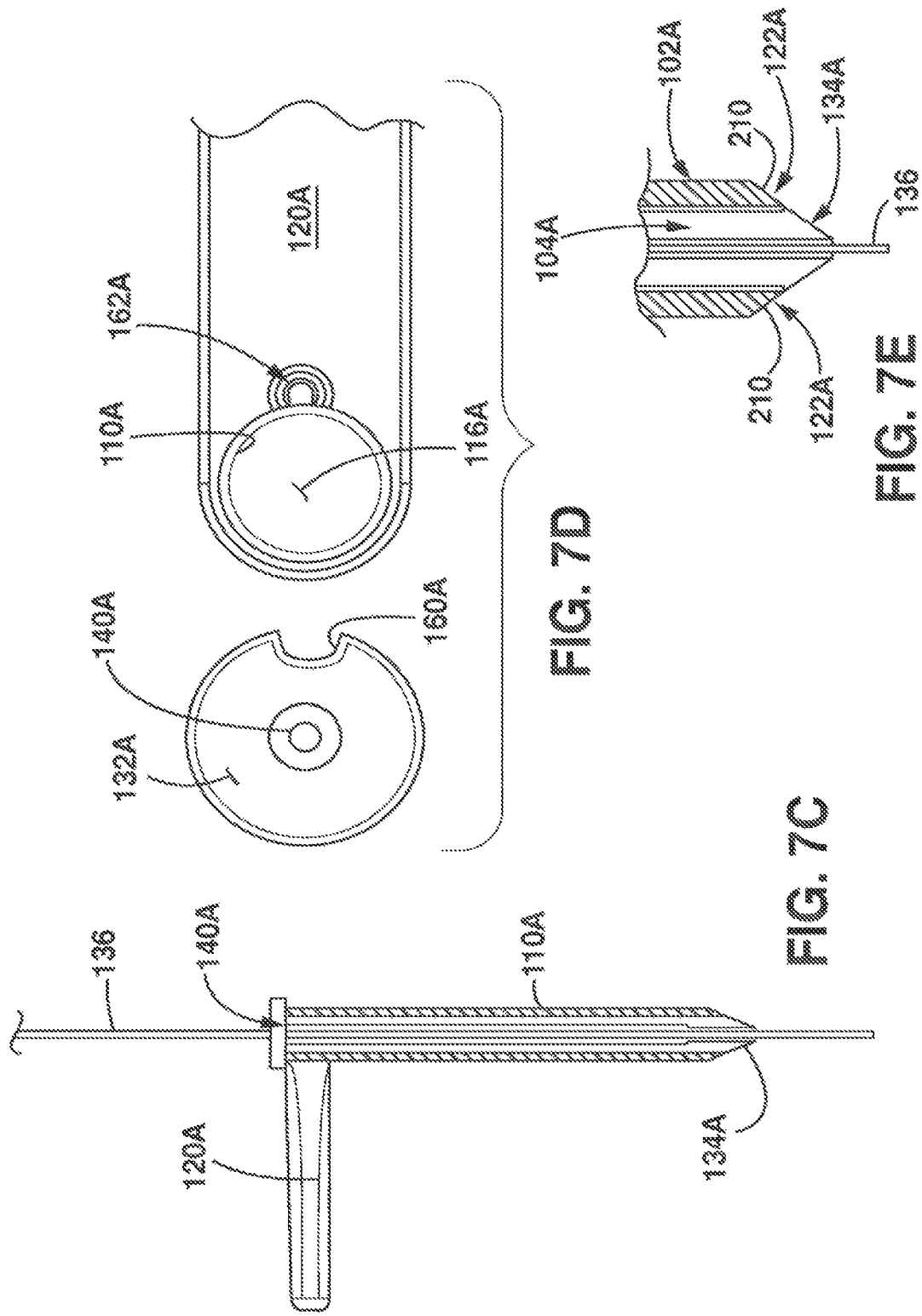

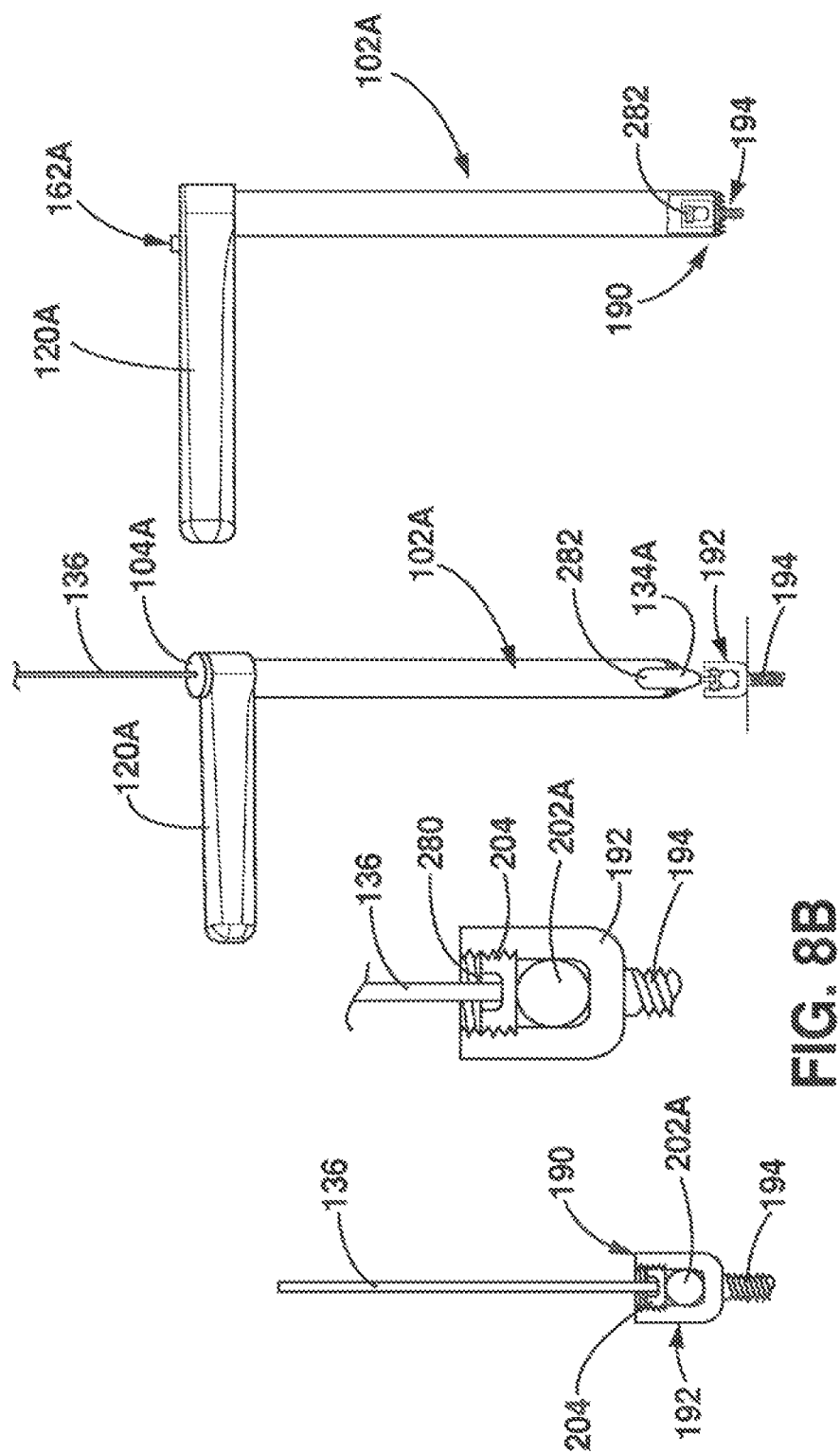

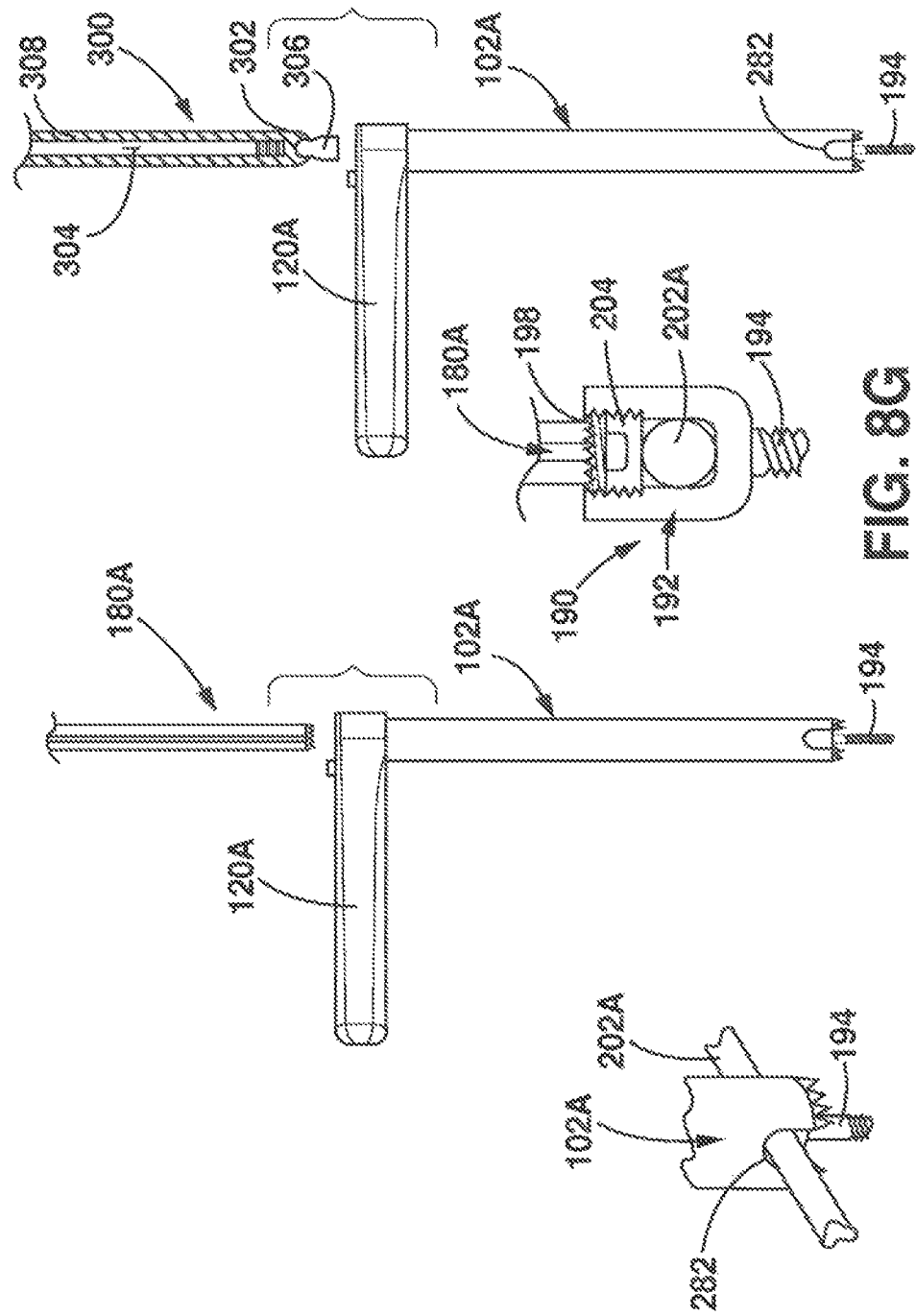

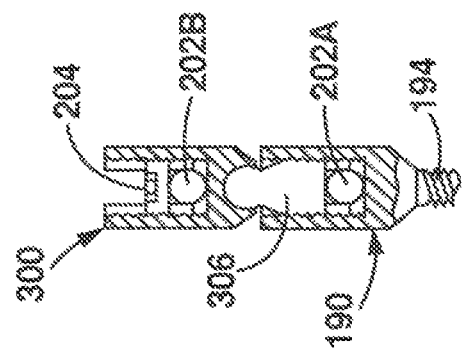
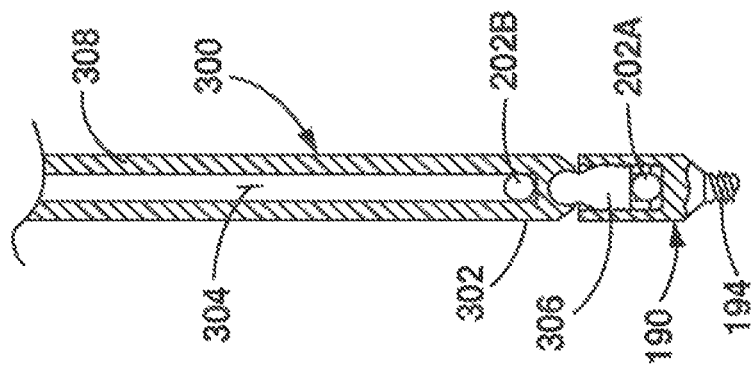

SURGICAL TOOLS HAVING APPLICATION FOR SPINAL SURGICAL PROCEDURES AND METHOD OF USE

The present application is a National Phase entry of PCT Application No. PCT/US2016/061535, filed Nov. 11, 2016, which is a continuation of U.S. patent application Ser. No. 14/941,046, filed Nov. 13, 2015, which are incorporated herein by reference in their entirety.

BACKGROUND

Minimally invasive surgical techniques and tools have developed to treat spinal conditions such as spinal instability and deformities. Minimally invasive techniques use small incisions to access a treatment site. Such techniques reduce blood loss, postoperative pain and reduce recovery time. Dilator tubes are typically used to provide a path or conduit to a treatment site. During the course of surgery, many different instruments will be used to perform different tasks or functions. The different instruments are inserted to the treatment site using the path or conduit provided by one or more dilator tubes. Insertion of multiple instruments can complicate the surgical process and increase the time required to complete the surgical procedure.

SUMMARY

The present application relates to tools having application for minimally invasive surgery and in particular minimally invasive spinal surgery. In embodiments described, the tools include a cannula tool having an elongate tubular body forming a passage lumen extending through the elongate tubular body. The cannula tool is used with a piercing tool to open a path to a treatment site. The cannula tool includes cutting teeth to roughen and decorticate bone for the surgical procedure. In an illustrated embodiment, a decorticator tool is sized for insertion into the passage lumen of the cannula tool for use in combination with the cannula tool to remove bone. In another embodiment, the cannula tool is used with a plunger tool to form a material delivery device or instrument to inject bone fusion or grafting material for spinal fusion. In embodiments described, the cannula tool includes an interlocking element which interfaces with an interlocking element on another tool inserted into the passage lumen of the cannula tool to control and manipulate the inserted tool in combination with the cannula tool. For an illustrated surgical application, the piercing tool has an asymmetric piercing tip and the piercing and plunger tools have asymmetric guide lumens for placement proximate to a treatment site.

In an illustrated aspect, the application provides a cannula tool having an elongate tubular body forming a passage lumen having an inlet at a proximal end of the tubular body and an outlet at a distal end; and a piercing tool having an elongate cylindrical body sized for insertion into the passage lumen of cannula tool and the elongate cylindrical body and the cannula tool including interlocking elements to rotationally connect the piercing and cannula tools for insertion and the cylindrical body having a proximal end and a distal end having a piercing tip and the piercing tool including a guide lumen for insertion of the combination of the piercing tool and the cannula tool over an anchored guide wire to insert the cannula tool through the body to a treatment site.

In another aspect, the application provides an asymmetrical piercing tool formed of an elongate cylindrical body having an enlarged head at a proximal end and a distal piercing tip asymmetrically tapered to form a terminus at an outer diameter of the elongate cylindrical body and the elongate cylindrical body having an asymmetric guide lumen for insertion of the piercing tool over a guide wire to a treatment site, the guide lumen having an inlet at the proximal end and an outlet at the terminus of the asymmetrical piercing tip.

In another aspect, the application provides a surgical instrument including a cannula tool having an elongate tubular body forming a passage lumen having an inlet at a proximal end of the tubular body and an outlet at a distal end of the tubular body and a plurality of cutting teeth spaced about the passage lumen at the distal end of the tubular body and a plunger tool having an elongate cylindrical body having a proximal end and a distal end and an outer diameter sized for insertion through the passage lumen of cannula tool and the plunger tool having a guide lumen for insertion over an anchored guide wire.

In another aspect, the application provides a surgical instrument including a cannula tool having an elongate tubular body forming a passage lumen having an inlet at a proximal end of the tubular body and an outlet at a distal end of the tubular body and a plurality of cutting teeth spaced about the passage lumen at the distal end of the tubular body and a decorticator tool sized for insertion through the passage lumen of cannula tool for use in combination with the cannula tool to decorticate bone.

In another aspect, the application provides a cannula tool and piercing tool having a tapered profile to provide a means for inserting the cannula tool and piercing tool though muscle fiber to a treatment site. In an embodiment shown, the tapered profile includes a pointed or tapered piercing tip and inwardly tapered teeth on the cannula tool to provide a means for minimizing damage to muscle tissue as the cannula tool and piercing tool are inserted to the treatment site. As described, the application includes a cannula tool having a plurality of inwardly tapered teeth and a piercing tool having a tapered piercing tip and guide lumen for insertion and placement of the cannula tool at a treatment site.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 1C is a cross-sectional view of the cannula and piercing tool shown with the piercing tool inserted into a passage lumen of the cannula tool.

FIG. 1D illustrates an embodiment of the piercing tool having an asymmetric guide lumen.

FIG. 1E is a cross-sectional view as taken along line 1E-1E of FIG. 1D.

FIG. 1F is a detailed illustration of the asymmetric tip of the piercing tool.

FIGS. 2A-2K progressively illustrate surgical steps utilizing the tools illustrated in FIGS. 1A-1F.

FIGS. 3A-3C illustrate an embodiment of cutting teeth on the cannula tool illustrated in FIG. 1A where FIG. 3C is a cross-sectional view taken along line 3C-3C of FIG. 3B.

FIGS. 4A-4B illustrate an embodiment of a decorticator tool for use with the cannula tool as illustrated in FIGS. 2D-2E.

FIGS. 7A-7C illustrate another embodiment of a cannula tool and piercing tool for surgical applications FIG. 7D illustrates interlocking elements on the cannula and piercing tools of FIGS. 7A-7C.

FIG. 7E is a detailed cross-sectional view of a distal portion of the cannula and piercing tools of FIGS. 7A-7C.

FIGS. 8A-8J illustrate process steps for utilizing the tools illustrated in FIGS. 7A-7C.

The following drawings illustrate embodiments of the present application and are not necessarily drawn to scale.

DETAILED DESCRIPTION OF ILLUSTRATIVE EMBODIMENTS

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Spinal surgical procedures are used to correct spinal conditions and deformities. Such surgical procedures include bone fusion techniques to fuse adjacent vertebrae. The fusion process involves deployment of bone grafting material to fuse facet joints of adjacent vertebrae. During the procedure the facet bones of adjacent vertebrae are decorticated to expose the spongy bone below the cortical layer. A bone grafting material is delivered to the decorticated vertebrae to stimulate bone growth to fuse the vertebrae. In addition to the fusion process, rods are typically placed along the spine or vertebrae to stabilize the spine while the facet bones of adjacent vertebrae fuse together. Recovery from the surgery depends upon the incisions and methods used to access the spine and techniques used to stabilize and fuse the spine. Minimally invasive surgical procedures have developed for different surgeries to reduce the time in surgery as well as recovery time for the patient.

Figure 1B:
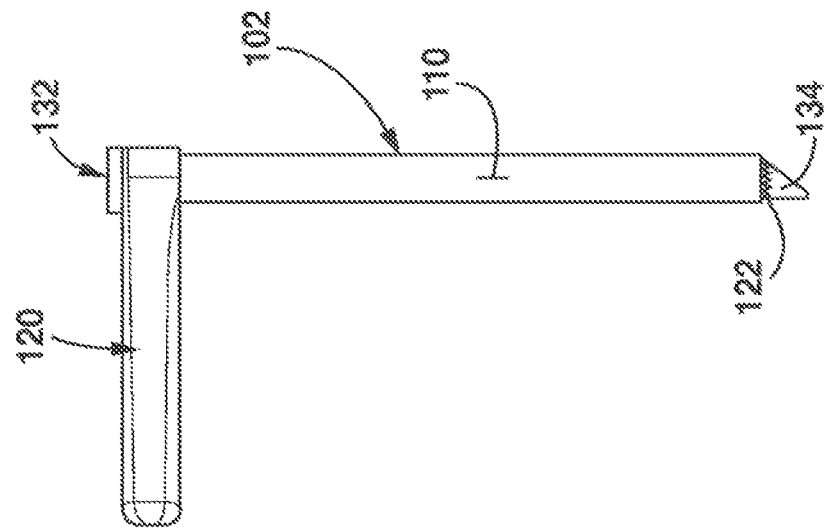
FIGS. 1A-1B illustrates a cannula tool and a piercing tool for accessing a treatment site for a surgical procedure.
Figure 1A:
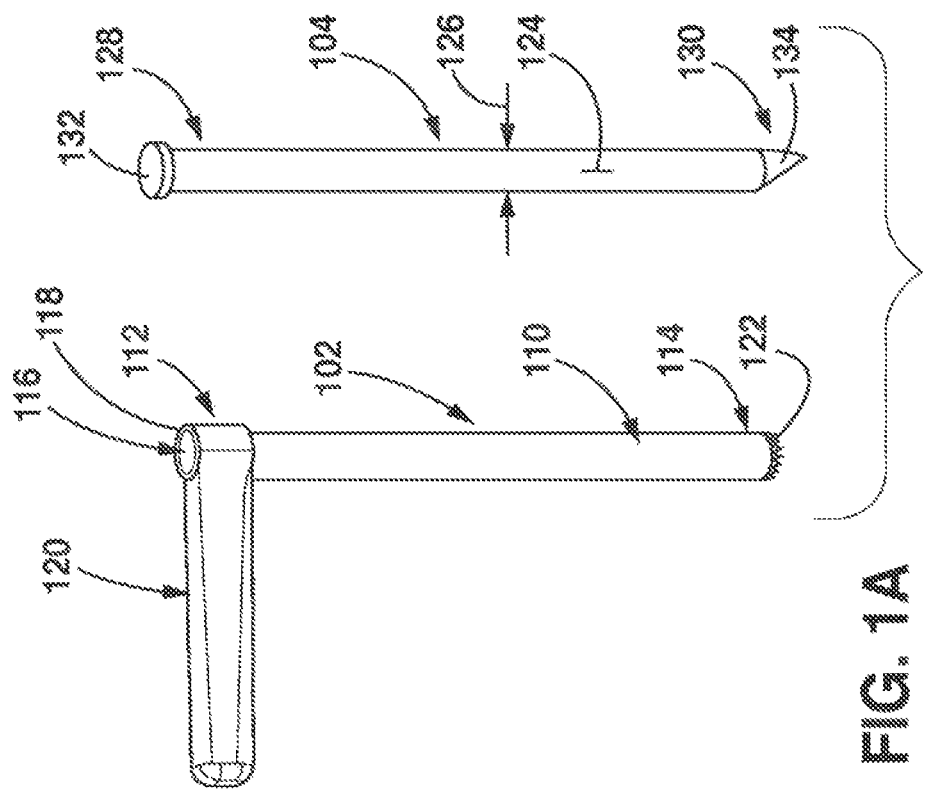

The present application relates to tools to simplify the surgical process and provide minimally invasive access and treatment for spinal conditions. The tools include a cannula tool 102 and a piercing tool 104 for placement of the cannula tool 102 at a treatment site. As illustrated in FIG. 1A, the cannula tool 102 includes an elongate tubular body 110 having a proximal end 112 and a distal end 114 and elongate passage lumen 116 enclosed via a cylindrical wall 118 extending between the proximal and distal ends 112, 114 of the tubular body 110. A handle 120 is connected to the proximal end of the elongate tubular body 110 for control and manipulation of the tool 102. In the illustrated embodiment, the cannula tool 102 also includes cutting teeth 122 at the distal end 114 for use to decorticate bone as described below.

The piercing tool 104 is formed of an elongate cylindrical body 124 having an outer diameter dimension 126 and length extending between a proximal end 128 and distal end 130. The outer diameter dimension 126 of the piercing tool 104 is sized for insertion through the passage lumen 116 of the cannula tool 102 as shown in FIG. 1B. As shown, the proximal end 128 of the piercing tool 104 includes an enlarged head 132 and the distal end of the piercing tool includes a piercing tip 134. The enlarged head 132 has a larger diameter than the passage lumen 116 (and the cylindrical body 124) to restrict insertion of the head 132 of piercing tool 104 into the passage lumen 116 of the cannula tool 102. In illustrated embodiments, the length of the piercing tool 104 is sized so that in the fully inserted position, the piercing tip 134 extends beyond an outlet or distal end 114 of the cannula tool 102.

The piercing tool 104 is inserted into the passage lumen 116 of the cannula tool 102 as shown in FIG. 1C. The tools 102, 104 are inserted over a Kirschner (K) or guide wire 136 to open a path through muscle for access to a treatment site. The tools 102, 104 are inserted over the K wire 136 through a guide lumen 140 formed along a length of the piercing tool as shown in FIG. 1D. The guide lumen 140 is an asymmetric channel formed along an outer perimeter of the cylindrical body 124. Illustratively, the cylindrical body 124 is formed of a solid body or a hollow body structure having sufficient column strength. As shown in FIG. 1E, the asymmetrical channel 140 is formed along an indented perimeter surface 142 along the length of cylindrical body 124. The piercing tip 134 has an asymmetrically tapered body 144 and terminus or pointed tip 146 as shown in FIGS. 1D and 1F and the guide lumen 140 or channel extends through the head 132 of the piercing tool 104 to the terminus or pointed tip 146.

Figure 1G:
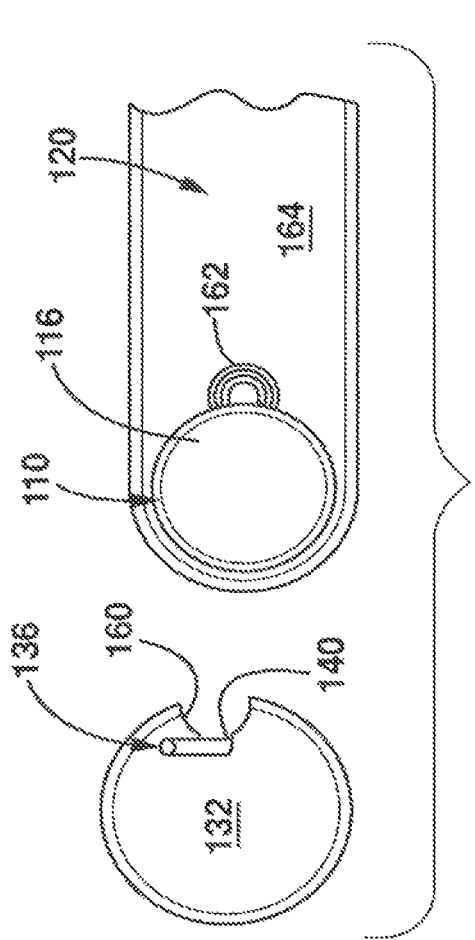
FIGS. 1G-1H illustrate interlocking elements to rotationally connect the cannula tool and the piercing tool.
Figure 1H:
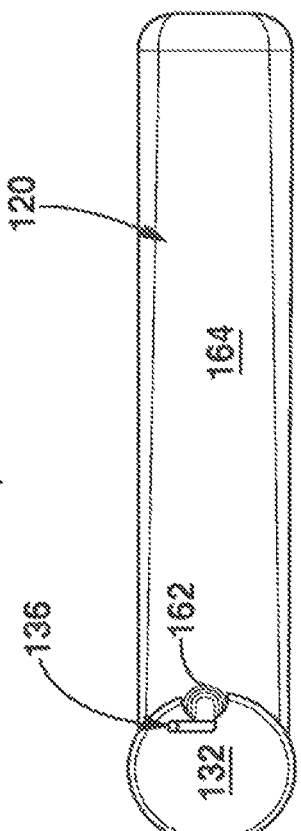

As shown in FIG. 1D, the head 132 of the piercing tool 104 includes a locking aperture 160 that interfaces with a locking pin 162 on the cannula tool 102 to rotationally lock the piercing tool 104 with rotation of the cannula tool 102 as shown in FIGS. 1G-1H. In the embodiment shown, the locking pin 162 is formed on an upper surface 164 of the handle 120. The guide lumen or channel 140 extends through the head of the piercing tool 104 and is opened to the locking aperture 160. The locking elements 160, 162 on the piercing tool 104 and cannula tool 102 provide threadless locking elements to impart rotation to the piercing tool 104 through rotation of the cannula tool 102. Thus, as shown, rotation of the cannula tool 102 is imparted to the piercing tool 104 via contact of the pin 162 with head 132 of the piercing tool 104. Thus, placement of the piercing tool 104 is controlled through handle 120 of the cannula tool 102. It should be understood that application is not limited to a particular arrangement, design or placement of the locking elements nor placement of the pin 162 on the cannula tool 102 and the aperture 160 on the piercing tool 104. Illustratively, the tubular body 110 and cylindrical body 124 of tools 102, 104 are formed of a surgical stainless steel or other material that can be sterilized for multiple use applications.

FIGS. 2A-2E progressively illustrate surgical steps utilizing the tools 102, 104 shown FIGS. 1A-1H. As shown in FIG. 2A, the K wire 136 is inserted and anchored at a treatment site 170. Illustratively, the treatment site 170 is proximate to a pedicle bone and facet joints between adjacent vertebrae or alternate treatment site. As will be appreciated by those skilled in the art, the K-wire is a slender rod with a sharp needle-like tip. The K-wire 136 is inserted into the patient and advanced to the treatment site 170 using diagnostic imaging. The sharp tip of the K-wire 139 is anchored into the bone to secure the K-wire 136 for treatment. As shown in FIG. 2B, the cannula tool 102 and piercing tool 104 are then advanced over the K-wire 136 to the treatment site 170. As shown, the piercing tip 134 of the piercing tool 102 is used to pierce through muscle tissue to separate muscle to open a tunnel or conduit to the treatment site 170. The piercing tool 104 moves along the K-wire 136 for placement adjacent to the anchored K-wire 136. As shown the asymmetrically tapered body 144 of the piercing tip 134 provides a tapered surface extending from the pointed tip 146 to the outer diameter of the cannula tool 102 to provide a progressively larger outer diameter dimension for dilation and passage through the muscle tissue.

Thereafter as shown in FIG. 2C, the piercing tool 104 is removed from the passage lumen 116 of cannula tool 102. With the piercing tool 104 removed, the cutting teeth 122 of the cannula tool 102 can be used to remove cortical bone to expose the spongy bone below the cortical bone. In the embodiment shown in FIG. 2D, a decorticator tool 180 is inserted into the passage lumen 116 of the cannula tool 102 along the K-wire 136. The decorticator tool 180 includes rasping teeth 182 at a distal end. When inserted as shown in FIG. 2E, the combination of the rasping teeth 182 of the decorticator tool 180 with the cutting teeth 122 on the cannula tool 102 cooperatively decorticate bone via movement of the cannula tool 102 and decorticator tool 108 relative to the anchored K-wire 136.

With the decortication process complete, the decorticator tool 180 is removed from the cannula tool 102 and a plunger tool 185 is then inserted into passage lumen 116 of the cannula tool 102 to deliver bone grafting or other biological material to the treatment site. As diagrammatically shown in FIG. 2F, prior to insertion of the plunger tool 185, bone grafting material or other biological agent is inserted into the passage lumen 116 of the cannula tool 102. Thereafter the plunger tool 185 is inserted and advanced along the K-wire 136 through the passage lumen 116 of the cannula tool 102 to compress the grafting material to dispense the grafting material to the treatment site 170. Thus as shown, the cannula tool 102 forms a barrel of a material delivery instrument for injecting grafting material to the treatment site. In particular, the cannula tool 102 remains in place following decortication and forms the barrel of the material delivery instrument to reduce surgical steps.

In the embodiment shown, following deployment of the grafting or other biological material, the plunger tool 185 and the cannula tool 102 are removed for insertion of a pedicle screw 190 over the K-wire 136. As shown, the pedicle screw 190 is inserted to the treatment site over the K-wire 136. The pedicle screw 190 includes a head 192, a threaded portion 194 and an extension 196. The head 192 includes a threaded channel 198 to support a stabilizing rod of a stabilizing structure. At the treatment site, the screw 190 is threaded or tapped into the bone via a screw driver device (not shown) and the K-wire 136 is removed as illustrated in FIG. 2I. As illustrated in FIG. 2J, rod 202 is installed through extension 196 into the threaded channel 198 to assemble the stabilizing structure. Once the rod 202 is in place in the threaded channel 198, a set screw 204 is inserted through the extension 196 and fastened to the head of the pedicle screw 190 using known techniques to secure the rod 202 in the channel 198. As shown in FIG. 2K, once the set screw 204 is fastened, the extension 196 is removed leaving the pedicle screw 190 in place.

FIGS. 3A-3C illustrate an embodiment of the cutting teeth 122 at the distal end of the cannula tool 102. The teeth 122 are spaced about the cylindrical wall 118 at the distal end of the tubular body 110. The cutting teeth 122 are formed of a plurality of asymmetrically shaped teeth 122 including a sloped outer surface 210 and sloped side surfaces 212. The sloped outer surfaces 210 taper inwardly from an outer diameter of the tubular body 110 to a pointed tip 214 proximate to the inner diameter of the tubular body 110 to provide an inwardly tapered profile for insertion with the piercing tool 104. In particular as shown in FIG. 1F, the inwardly tapered surfaces 210 of the cannula tool 102 and tapered tip 134 of the piercing tool 104 provide a tapered profile to pass through muscle fibers for placement at the treatment site. The tapered profile as shown in FIG. 1F facilitates insertion of the cannula tool 102 and piercing tool 104 through the muscle fiber while limiting damage to muscle to provide a minimally invasive instrument or technique.

FIGS. 4A-4B illustrate an embodiment of the decorticator tool 180 shown in FIGS. 2D-2E. The tool 180 is formed of elongate body 222 having a generally cross-shaped cross-section and enlarged head 224 as shown in FIG. 4B. The cross-shape of the decorticator tool 180 provides a passage for the K-wire 136 along the length of the cannula tool 180 between the tool 180 and an inner diameter of the cannula tool 102. The decorticator tool 180 includes a plurality of teeth 226 at a distal end of the cross-shaped body 222 to remove bone. The head 224 of the decorticator tool 180 similarly includes a guide channel 228 for insertion of the K-wire 136 through the head 224 and aperture 160. The pin 162 on the cannula tool 102 engages the head 224 of the decorticator tool 180 through aperture 160 on the head 224 to rotationally lock the decorticator tool 180 with the cannula tool 102 for use to decorticate bone.

Figure 2G:
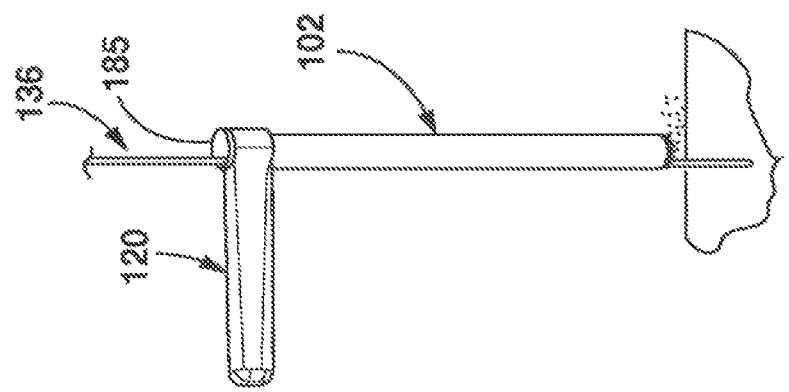
Figure 2F:
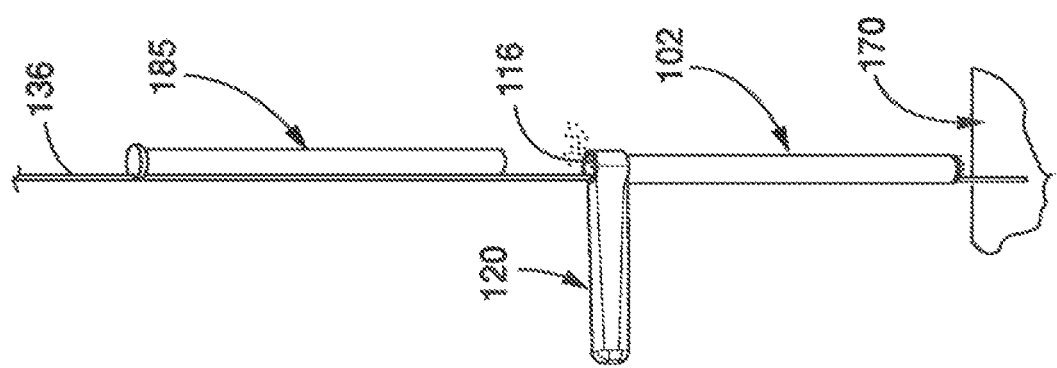
Figure 2E:
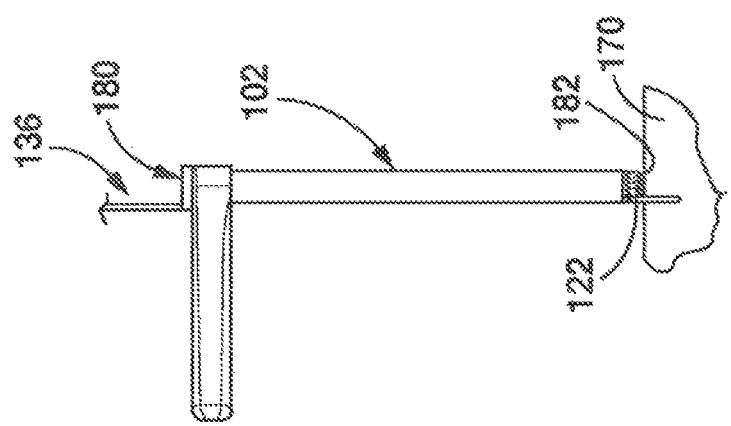
Figure 5A:
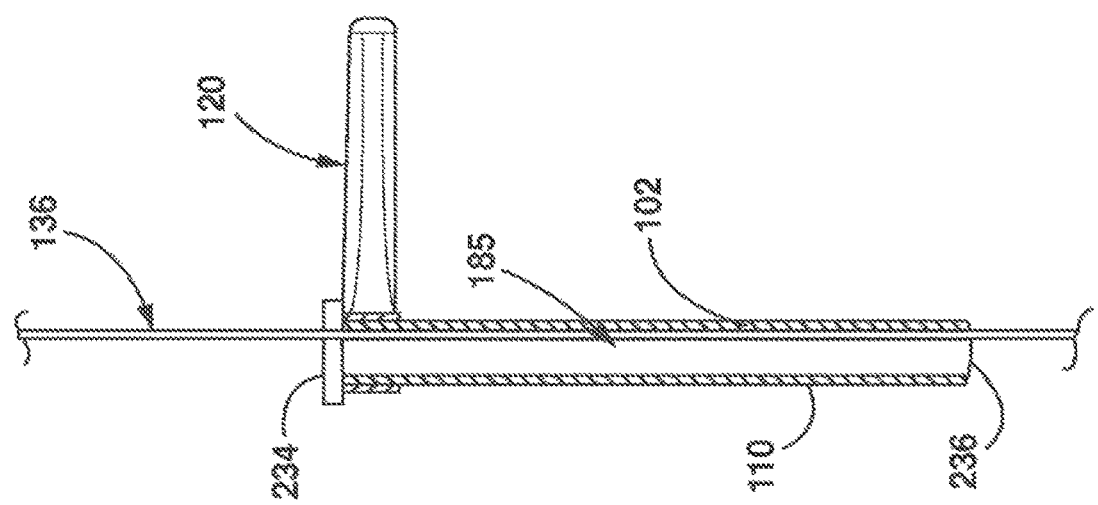
FIGS. 5A-5B illustrate an embodiment of the plunger tool for use with the cannula tool as illustrated in FIGS. 2F-2G.
Figure 5B:
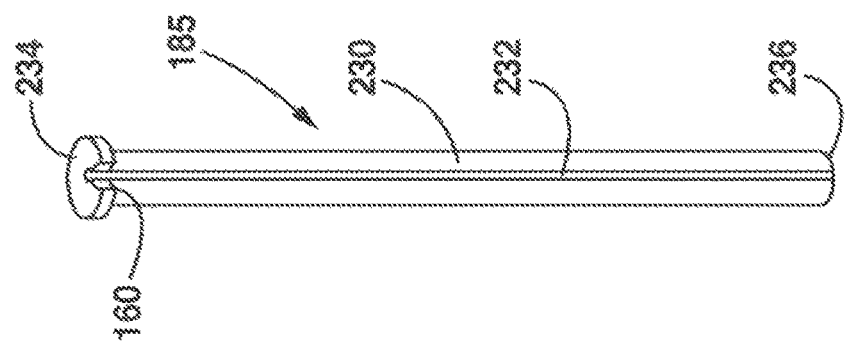

FIGS. 5A-5B, illustrate an embodiment of the plunger tool 185 shown in FIGS. 2F-2G. As shown, the plunger tool 185 is formed of an elongate cylindrical body 230 having an asymmetric guide lumen 232 similar to the piercing tool 104. The guide lumen 232 is formed of an opened channel along an outer diameter of cylindrical body 230 of the plunger tool 185 to insert the plunger tool into the cannula tool 102 over the K-wire 136. Similar to the piercing tool 104, the plunger tool 185 has an enlarged head 234 at a proximal end of the cylindrical body 230 and a blunt surface 236 at a distal end of the cylindrical body 230. The guide lumen 232 extends through the head 234 along the entire length of the cylindrical body 230 of the tool 185 similar to piercing tool 104. As shown, the head 234 of the plunger tool 185 similarly includes locking aperture 160 to interface with the locking pin 162 on the handle 120 to impart rotation for control of the plunger tool 185 in cooperation with the cannula tool as previously described.

As shown in FIG. 5B, in a fully inserted position, the head 234 of the plunger tool 185 abuts the top of the tubular body 110 of the cannula tool 102. The length of the cylindrical body 230 of the plunger tool 185 corresponds to the length of the tubular body so that the blunt surface 236 abuts a distal end of the cannula tool 102. The head 234 of the plunger 185 provides a relatively flat surface for use of a mallet to compact grafting material and inject bone grafting material to the treatment site using force. Thus, as shown the tubular body 110 of the cannula tool 102 forms the barrel for the material delivery device to inject the grafting material or other biological agent.

Figure 6A:
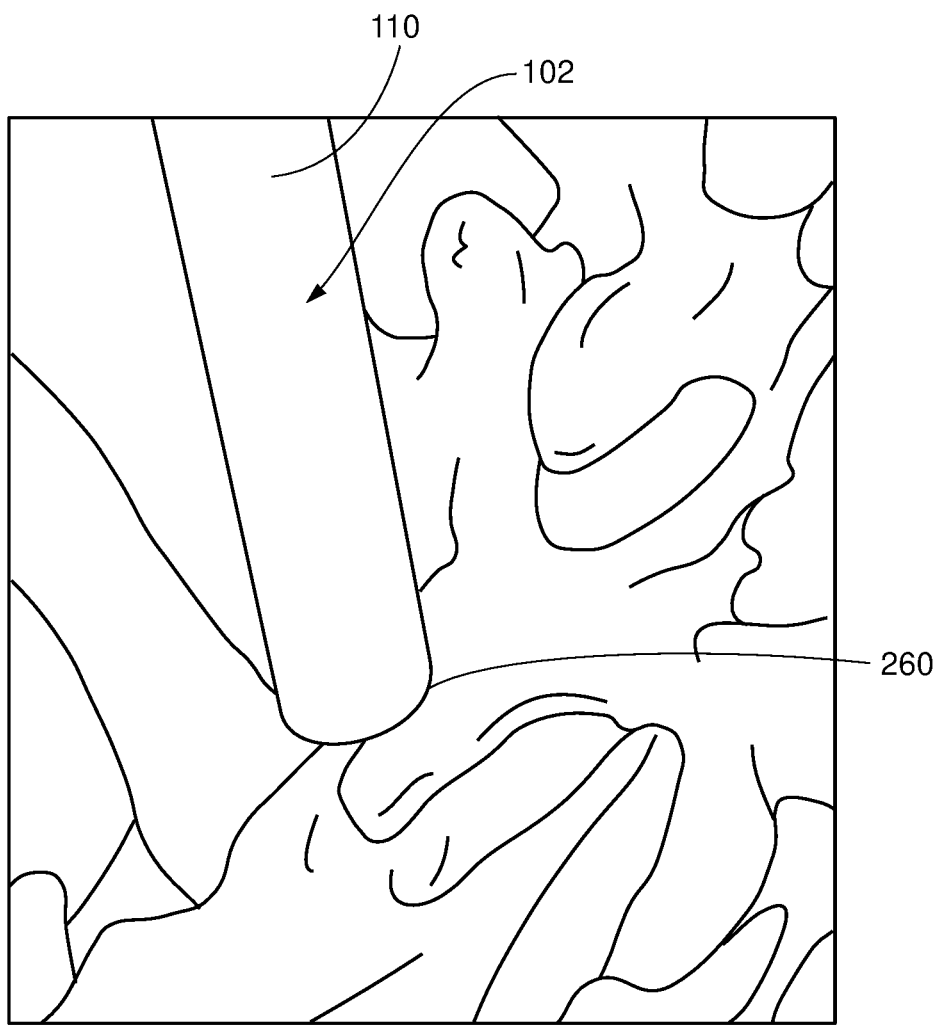
FIG. 6A illustrates placement of the cannula tool at the treatment site and FIG. 6B illustrates the cannula tool with the piercing tool removed.

In an illustrated embodiment, the elongate tubular body 110 of the cannula tool 102 has a length of approximately 170 mm and an inner diameter of the elongate tubular body 110 is larger than an outer diameter of the head 192 of pedicle screw 190. In one embodiment, the elongate tubular body 110 has an inner diameter dimension of 13 millimeters (mm) and a cylindrical wall thickness of 1 mm. For placement of the pedicle screw 190, the K-wire (not shown) is anchored in the pedicle bone shown in FIG. 6A. Use of the asymmetrical piercing tool 104 and plunger tool 185 positions the cannula tool 102 lateral of the anchored position of the K-wire to align the tools proximate to the facet joint 260 to decorticate bone using the decorticator tool 180 and deliver material to fuse the bone using the plunger tool 185. As shown, a diameter of the cannula tool 102 is sized so that cutting teeth 122 reach facet joint 260.

Figure 6B:
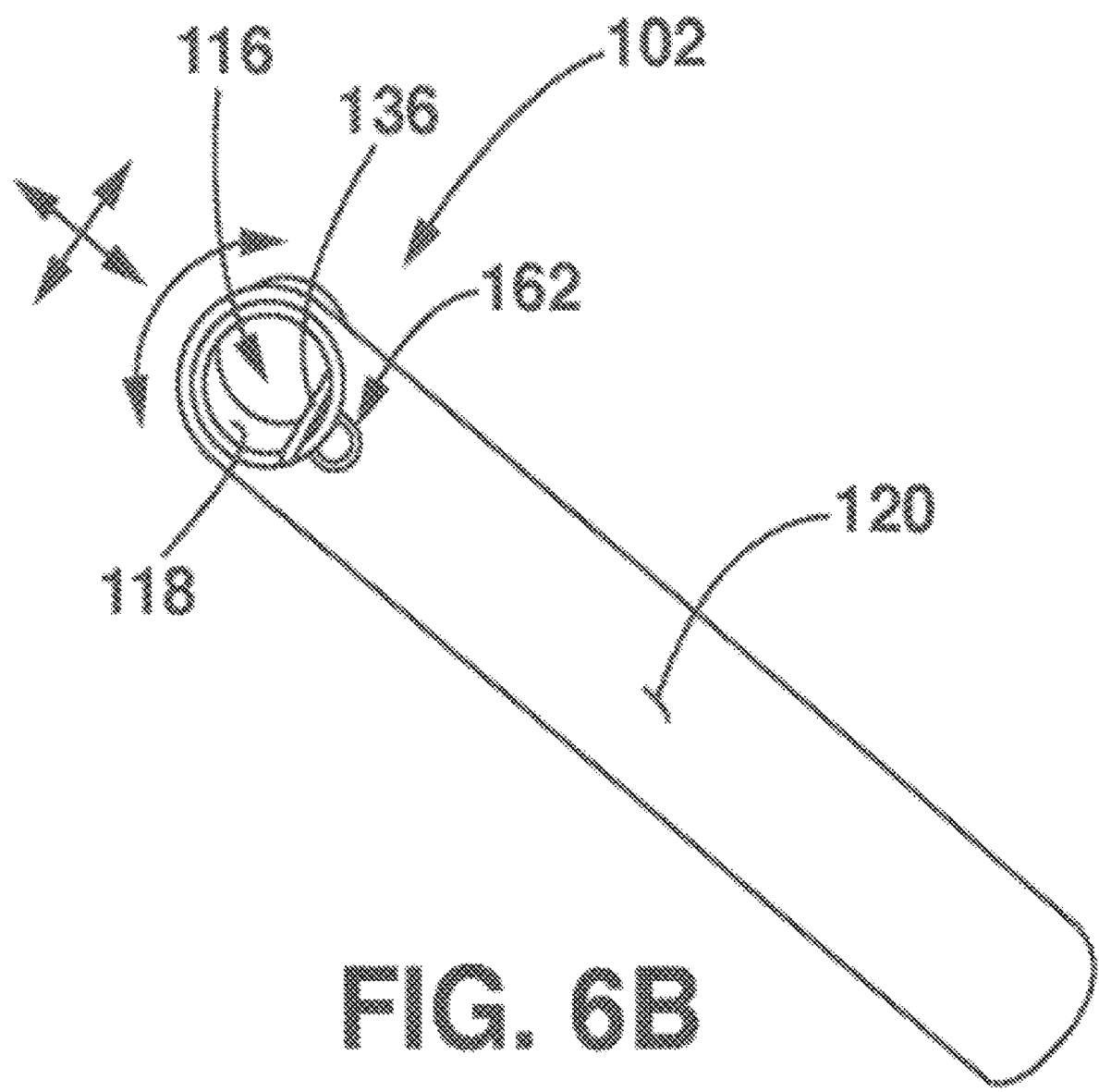

FIG. 6B illustrates the cannula tool 102 with the piercing tool 104 removed. With the piercing tool 104 removed, the cannula tool 102 can be moved in various directions as illustrated by arrows shown in FIG. 6B to provide a relatively large reach area to decorticate bone proximate to the facet joint. As previously described, the decorticator tool 180 is inserted to remove bone proximate to the facet joint 260 to prepare the site for the grafting material deployed using the asymmetrical plunger tool 185.

FIGS. 7A-7D illustrates another embodiment of a cannula tool 102A and piercing tool 104A for different applications. In the embodiment shown, the cannula tool 102A includes an elongate tubular body 110A, handle 120A and cutting teeth 122A similar to the cannula tool 102 described in FIGS. 1A-1B. The piercing tool 104A is formed of an elongate cylindrical body 124A having an outer diameter dimension 126A for insertion through the passage lumen 116A of the cannula tool 102A. A proximal end 128A of the piercing tool 104A includes enlarged head 132A and the distal end of the piercing tool includes a symmetric piercing tip 134A. In the embodiment shown, the piercing tip 134A is formed of a symmetrically tapered body having a centered pointed tip 146A.

The elongate cylindrical body 124A has a central guide lumen 140A formed of a centered longitudinal channel that extends through the head 132A to the pointed tip 146A symmetrically aligned with the center axis of the cylindrical body 124A for insertion of the piercing tool and cannula tool 102A over the K-wire 136 as illustrated in cross-section in FIG. 7C. As shown in FIG. 7D, the symmetric piercing tool 104A similarly includes an aperture 160A on the head 132A to interface with pin 162A on the cannula tool 102A to rotationally connect the piercing tool 104A and cannula tool 102A for coordinated movement (and rotation). The centered longitudinal channel can have multiple diameter portions and application is not limited to a particular lumen construction.

FIG. 7E illustrates a tapered profile for the distal ends of the piercing tool 104A and cannula tool 102A. As shown, the distal end of the cannula tool 102A includes inwardly tapered surfaces 210 formed via the cutting teeth 122A spaced about the passage lumen 116A of the cannula tool 102A. The inwardly tapered surfaces 210 of the cannula tool 102A and tapered piercing tip 134A of the piercing tool 104A provide a tapered profile to pass through muscle fibers for placement at the treatment site as previously described.

FIGS. 8A-8K illustrate use of the cannula 102A and piercing tool 104A to install a "piggy back" screw for a supplemental stabilizing rod structure. As shown in FIG. 8A, K-wire 136 is inserted into the patient and tracked using imaging techniques to an anchored pedicle screw 190 supporting a first rod 202A of an existing stabilizing structure. The K-wire 136 is tracked so that the tip of the K-wire 136 is supported in a channel 280 of set screw 204 as shown in FIG. 8B. Thereafter, the cannula and piercing tools 102A, 104A are inserted over the K-wire 136 to the pedicle screw 190 as shown in FIG. 8C. Once the cannula tool 102A is inserted to the pedicle screw 190, the piercing tool 104A and K-wire 136 are removed as illustrated in FIG. 8D. As shown, the inner diameter of the cannula tool 102A is larger than an outer diameter of the head 192 of the pedicle screw 190 to fit over the head 192 of the pedicle screw 190. The distal end of the cannula tool 102A includes diametrically opposed cut-outs 282 also shown in FIG. 7A sized to fit over rod 202A. The cannula tool 102A is advanced over the head 192 of the screw 190 to surround the head 192 of the screw 190 to remove debris as illustrated in FIG. 8E. The cut-outs 282 allow the cannula tool 102A to slide over the head 192 of the screw without interference of rod 202A.

As shown in FIG. 8F, decorticator tool 180A is inserted into the cannula tool 102A to remove debris over the set screw 204. The decorticator tool 180A described is similar to decorticator tool 180 except that the profile of the cross-shaped body is smaller and sized to fit in the channel 198 of the pedicle screw to remove debris and bone growth over the set screw 204 as illustrated in detail in FIG. 8G. The head (not shown) of the decorticator tool 180A is sized to abut the distal end of the cannula tool 102A and rotationally lock to the cannula tool 102A via interfacing locking elements as previously described with respect to decorticator tool 180A. In alternative embodiments, the elongate body of the decorticator tool 180A has multiple sections to provide a smaller profile dimension at the distal end for insertion into the channel 198 of the pedicle screw 190 to remove debris.

Once the debris is removed, the decorticator tool 180A is removed from the cannula tool 102A. The set screw 204 is removed via a screw driver inserted through the cannula tool. (not shown). A piggy back screw 300 is then inserted through the passage lumen 116A of cannula tool 102A for placement at the treatment site as illustrated in FIG. 8H. The piggy back screw 300 includes a head portion 302 with threaded channel 304, a threaded connector 306 and extension 308 for installing a second rod 202B for the supplemental stabilizing structure. The piggy back screw 300 is inserted through the cannula tool 102A to thread connector 306 into the threaded channel 198 of the pedicle screw 190 to connect the piggy back screw 300 to the pedicle screw 190. In FIG. 8I, the cannula tool 102A is removed and the second rod 202B is installed in threaded channel 304 through extension 308. The set screw 204 is inserted into the threaded channel 304 and tightened to connect the second rod 202B to the piggy back screw 300 anchored in the bone through pedicle screw 190 and the extension 308 is removed as illustrated in FIG. 8J. In the illustrated embodiment piggy back screw 300 has a pivot joint (not numbered) between threaded connector 306 and head portion 302 to adjust alignment of the piggy back screw 300 relative to the pedicle screw 190. It should be understood that although a particular pedicle screw 190 and piggy back screw 300 are shown, application is not limited to the particular embodiments shown.

In illustrated embodiments, the tools 100 are used to access, decorticate and deliver material to fuse facet joints of adjacent vertebrae. As described, the cannula tool 102 or 102A is used in combination with additional tools to provide the multiple instruments necessary for a spinal fusion procedure. In particular, as described, the piercing and cannula tools 102, 104, 102A, 104A are used to open a path to the treatment site. Once the piercing tool 104, 104A has located the treatment site the piercing tool 104, 104A is removed for use of the cannula tool 102A. 102B with other tools including the plunger and decorticator tools 180, 180A, 185 as described.

While illustrated embodiments of the tools have been described, application is not limited to the particular embodiments described. In particular, the features and tools described in the present application can be used for different applications or can be combined in different combinations as will be appreciated by those skilled in the art. Additionally although a particular handle shape or contour is shown, it should be understood that application is not limited to the particular shape and design shown. Further, although the application describes use of a K-wire, it should be appreciated by those skilled in the art that any similar guide wire device can be used to guide the tools to the treatment site.

What is claimed:

1. A method comprising:
   inserting a cannula tool having a piercing tool in a passage lumen of the cannula tool over a guide wire anchored in bone at a treatment site, the cannula tool including a plurality of cutting teeth;
   advancing the cannula and piercing tool combination along the guide wire for placement at the treatment site;
   withdrawing and removing the piercing tool from the cannula tool; and
   applying one or more treatments using the cannula tool at the treatment site,
   wherein the step of applying one or more treatments includes moving the cannula tool relative to the anchored guide wire to decorticate bone at the treatment site with the plurality of cutting teeth.

2. The method of claim 1 and comprising the steps of:
   inserting a decorticator tool having a plurality of rasping teeth through the passage lumen of the cannula tool over the guide wire to the treatment site; and
   moving the cannula and decorticator tool in combination to decorticate bone at the treatment site.

3. The method of claim 1 and following the step of moving the cannula tool to decorticate bone at the treatment site comprising the steps of:
   inserting a biological agent or grafting material into the passage lumen of the cannula tool; and
   inserting a plunger tool into the passage lumen of the cannula tool and advancing the plunger tool over the guide wire towards a distal end of the passage lumen to dispense the biological agent or grafting material from the cannula tool to the treatment site.

4. The method of claim 3 and following the step of dispensing the biological agent or grafting material comprising the steps of:
   removing the cannula tool and the plunger tool from a patient;
   inserting a pedicle screw over the guide wire to the treatment site; and
   anchoring the pedicle screw in the bone.

5. A method comprising:
   inserting a cannula tool having a piercing tool in a passage lumen of the cannula tool over a guide wire anchored at a treatment site;
   advancing the cannula and piercing tool combination along the guide wire for placement at the treatment site, the guide wire being withdrawn with the piercing tool;
   withdrawing and removing the piercing tool from the cannula tool; and
   applying one or more treatments using the cannula tool at the treatment site, the one or more treatments including:
      inserting a decorticator tool into the passage lumen of the cannula tool;
      removing debris from a pedicle screw anchored into a pedicle bone;
      removing the decorticator tool and set screw on the pedicle screw;
      inserting a "piggy back" screw through the cannula tool; and
      connecting the "piggy back" screw to the pedicle screw.

\* \* \* \* \*